(12) United States Patent
Davids et al.

(10) Patent No.: US 12,066,511 B2
(45) Date of Patent: Aug. 20, 2024

(54) METHOD FOR DESIGNING ELECTROMAGNETIC COILS WITH EXPLICIT PERIPHERAL NERVE STIMULATION CONSTRAINT BASED ON AN ORACLE PENALTY

(71) Applicant: THE GENERAL HOSPITAL CORPORATION, Boston, MA (US)

(72) Inventors: Mathias Davids, Manheim (DE); Bastien Guerin, Cambridge, MA (US); Lawrence L. Wald, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 198 days.

(21) Appl. No.: 17/442,808

(22) PCT Filed: Mar. 26, 2020

(86) PCT No.: PCT/US2020/024936
§ 371 (c)(1),
(2) Date: Sep. 24, 2021

(87) PCT Pub. No.: WO2020/198460
PCT Pub. Date: Oct. 1, 2020

(65) Prior Publication Data
US 2022/0179022 A1 Jun. 9, 2022

Related U.S. Application Data

(60) Provisional application No. 62/824,591, filed on Mar. 27, 2019.

(51) Int. Cl.
*G01G 3/00* (2006.01)
*A61N 2/00* (2006.01)
(Continued)

(52) U.S. Cl.
CPC ......... *G01R 33/3858* (2013.01); *A61N 2/006* (2013.01); *A61N 2/02* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 8,860,414 B2  10/2014  Brereton et al.
2001/0007950 A1  7/2001  North et al.
(Continued)

FOREIGN PATENT DOCUMENTS

EP  1411367 B1  8/2012

OTHER PUBLICATIONS

Huang et al., The Optimized Scheme of Performance Parameters of Gradient Coils for Permanent Magnetic Open Architecture Nuclear Magnetic Resonance System, 2011 5th International Conference on Bioinformatics and Biomedical Engineering, 2011, pp. 1-5.
(Continued)

*Primary Examiner* — Walter L Lindsay, Jr.
*Assistant Examiner* — Frederick Wenderoth
(74) *Attorney, Agent, or Firm* — Quarles & Brady LLP

(57) ABSTRACT

Systems and methods for designing and manufacturing electromagnetic coils for use with a magnetic resonance imaging ("MRI") system are described. More particularly, described here are methods for designing and manufacturing gradient coils for producing magnetic field gradients with greater peripheral nerve stimulation ("PNS") thresholds relative to conventional gradient coils. The gradient coil design is constrained using an oracle penalty that is computed to account for a PNS requirement for the coil. In other applications, the oracle penalty can be used to optimize
(Continued)

driving patterns for an electromagnetic stimulation system, such that a target PNS requirement is achieved.

23 Claims, 6 Drawing Sheets

(51) Int. Cl.
*A61N 2/02* (2006.01)
*G01R 33/385* (2006.01)

(58) Field of Classification Search
USPC .......................................................... 324/318
See application file for complete search history.

(56) References Cited

U.S. PATENT DOCUMENTS

| | | |
|---|---|---|
| 2006/0015153 A1 | 1/2006 | Gliner et al. |
| 2014/0350634 A1 | 11/2014 | Grill et al. |
| 2016/0169997 A1* | 6/2016 | Fautz .................. G01R 33/543 324/309 |

OTHER PUBLICATIONS

Schluter et al., The Oracle Penalty Method, Journal of Global Optimization, 2010, 47:293-325.
PCT International Search Report and Written Opinion, PCT/US2020/024936, Jun. 22, 2020, 8 pages.

\* cited by examiner

METHOD FOR DESIGNING ELECTROMAGNETIC COILS WITH EXPLICIT PERIPHERAL NERVE STIMULATION CONSTRAINT BASED ON AN ORACLE PENALTY

CROSS-REFERENCE TO RELATED APPLICATIONS

This application is a U.S. National Stage of International Application No. PCT/US2020/024936 filed Mar. 26, 2020 which claims the benefit of U.S. Provisional Patent Application Ser. No. 62/824,591, filed on Mar. 27, 2019, and entitled "NUMERICAL OPTIMIZATION METHOD FOR CONTROL OF PERIPHERAL NERVE STIMULATION BY EXTERNALLY APPLIED FIELDS."

STATEMENT REGARDING FEDERALLY SPONSORED RESEARCH

This invention was made with government support under EB025121 and EB025162 awarded by the National Institutes of Health. The government has certain rights in the invention.

BACKGROUND

Peripheral nerve stimulation ("PNS") is the excitation of large nerves in the body by the application of an externally applied electromagnetic field. PNS is often accompanied by a physical sensation that can range from unpleasant to painful. The federal drug administration ("FDA") regulates the PNS sensation to disallow painful stimulation, which applies to all devices that have the potential to create PNS either by design or as an unwanted byproduct of the main device function. For example, PNS occurs in magnetic resonance imaging ("MRI") because of the switching gradient coils used to create the MRI image. Since the use of gradient coils cannot be avoided, by consequence PNS also cannot be avoided. However, the propensity and location of PNS for a given gradient field strength and switching frequency can be altered by alterations to the design of the gradient coil. Although the FDA guidelines are for the absence of painful sensation, MRI vendors typically set their use criteria to produce no more than a small unharmful tingling in a fraction of patients (and most feel nothing).

Over the years, MRI engineers have devised technology that allows for faster and faster switching of gradient magnetic fields. In fact, PNS, not engineering aspects of the MRI gradient coil manufacturing process, is often now the limiting factor of acquisition speed in MRI for many sequences and clinical applications. Overcoming the PNS limit would, therefore, result in faster imaging (reduced scan time) for many applications. For example, fast imaging sequences such as echo planar imaging could be run much faster, resulting in shorter scan time and, generally, a greater rate of data acquisition per unit time. This would be particularly helpful in functional MRI and diffusion MRI, where the acquisition of more data per second would allow better determination of functionally active areas of the brain and white mater pathways, respectively. In diffusion imaging, faster gradient switching without PNS would allow a greater data acquisition rate, a reduction of the echo time at constant diffusion encoding strength (the so-called "b-value"), and less noise and more signal. Another fast sequence that would greatly benefit from greater gradient switching speed without PNS is turbo-spin echo ("TSE"), which is a frequently used scan sequence in basic clinical MRI. In this case, faster gradient switching rates would result in shorter scan time and therefore greater patient throughput.

Another major advantage of an increase of the data acquisition rate in MRI, rendered possible by less stringent or absence of PNS constraints on the waveforms that can safely be played on the gradient system, is the reduction of the echo-time ("TE") at constant resolution. This reduction of the TE has two major advantages. First, it increases the signal-to-noise ratio ("SNR"). Therefore, reduction of TE in MRI generally leads to higher quality images with less noise, which is desirable for the diagnosis of many diseases as well as functional imaging, such as fMRI and arterial spin labeling. Second, a short TE minimizes a type of image distortion that is caused by the presence of non-uniform field regions in the field-of-view, which is generally unavoidable in MRI. Non-uniformity of the main magnetic field is mainly due to difference in susceptibility between regions of the body. For example, a region that is difficult to image because of this effect is the ear canals and the region right above the sinus in the head. There, the large difference in susceptibility between brain tissues and air (in the ear canal and sinuses) causes large field variations that in turn deform the image. This type of artifact is difficult to correct. It turns out that these deformations are proportional to the TE, so decreasing TE is highly beneficial.

There are other devices that are designed to create PNS on purpose. For example, implanted electrodes have been used in spinal cord stimulation to reduce chronic pain. Since then, a plethora of applications have been targeted using implanted or surface electrodes, such as occipital nerve stimulation for the treatment of migraines, pudendal nerve stimulation for the treatment of urinary bladder incontinence, and sciatic nerve stimulation for the treatment of back pain. Note that in many of these cases, PNS can in fact have a blocking effect and shut down the propagation of action potentials. Therefore, PNS can result either in the excitation or inhibition of peripheral nerves.

Devices that are designed to produce PNS are usually single-electrode systems that are placed close to the nerve of interest. For deep nerves, such as the sciatic nerve target in the treatment of back pain, this means that the electrode has to be surgically implanted. Using surface electrodes would be of interest, either to avoid a surgery or to assess the efficacy of a potential surgical implantation on a patient-specific basis in order to avoid a costly and dangerous surgery in non-responsive patients. In this case, what is needed are electrode arrays that are optimized in order to specifically target deep nerves. Other devices are magneto-stimulation coils placed over the nerve of interest. Again, an array of such devices, with properly optimized drive configurations, can potentially be much more effective at targeting specific nerves and for reaching deep nerves without widespread activation.

SUMMARY OF THE DISCLOSURE

The present disclosure addresses the aforementioned drawbacks by providing a method of manufacturing an electromagnet coil for use in a magnetic resonance imaging (MRI) system. The method includes computing a peripheral nerve stimulation (PNS) oracle penalty using a computer system, where the PNS oracle penalty includes a parameter representative of a PNS requirement for the electromagnetic coil. The method also includes setting a plurality of performance metric requirements for a plurality of performance metrics for the electromagnet coil using the computer system. A performance functional is formed using the computer system, where the performance functional is for generating a current density pattern over a coil surface for the electromagnetic coil. The performance functional is based on the plurality of performance metrics and the PNS oracle penalty. The performance functional is optimized based on the PNS requirement and the plurality of performance metric requirements using the computer system. A current density pattern is generated over the coil surface based on the optimized performance functional, and coil windings are obtained from the current density pattern. Other embodiments of this aspect include corresponding computer systems, apparatus, and computer programs recorded on one or more computer storage devices, each configured to perform the actions of the methods.

Another general aspect includes a method for controlling the operation of an electromagnetic stimulation system. The method includes computing a PNS oracle penalty using a computer system, where the PNS oracle penalty includes a parameter representative of a target nerve stimulation requirement for the electromagnetic stimulation system. The method also includes setting a plurality of performance metric requirements for a plurality of performance metrics for the electromagnetic stimulation system using the computer system. A performance functional is formed using the computer system, where the performance functional is for generating a stimulation driving pattern for the electromagnetic stimulation system. The performance functional is based on the plurality of performance metrics and the PNS oracle penalty. The performance functional is optimized based on the target nerve stimulation requirement and the plurality of performance metric requirements using the computer system, and a stimulation driving pattern based is generated based on the optimized performance functional. The stimulation driving pattern is applied to the electromagnetic stimulation system in order to generate an electromagnetic field that when applied to a subject causes the subject to receive nerve stimulation according to the target nerve stimulation requirement. Other embodiments of this aspect include corresponding computer systems, apparatus, and computer programs recorded on one or more computer storage devices, each configured to perform the actions of the methods.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
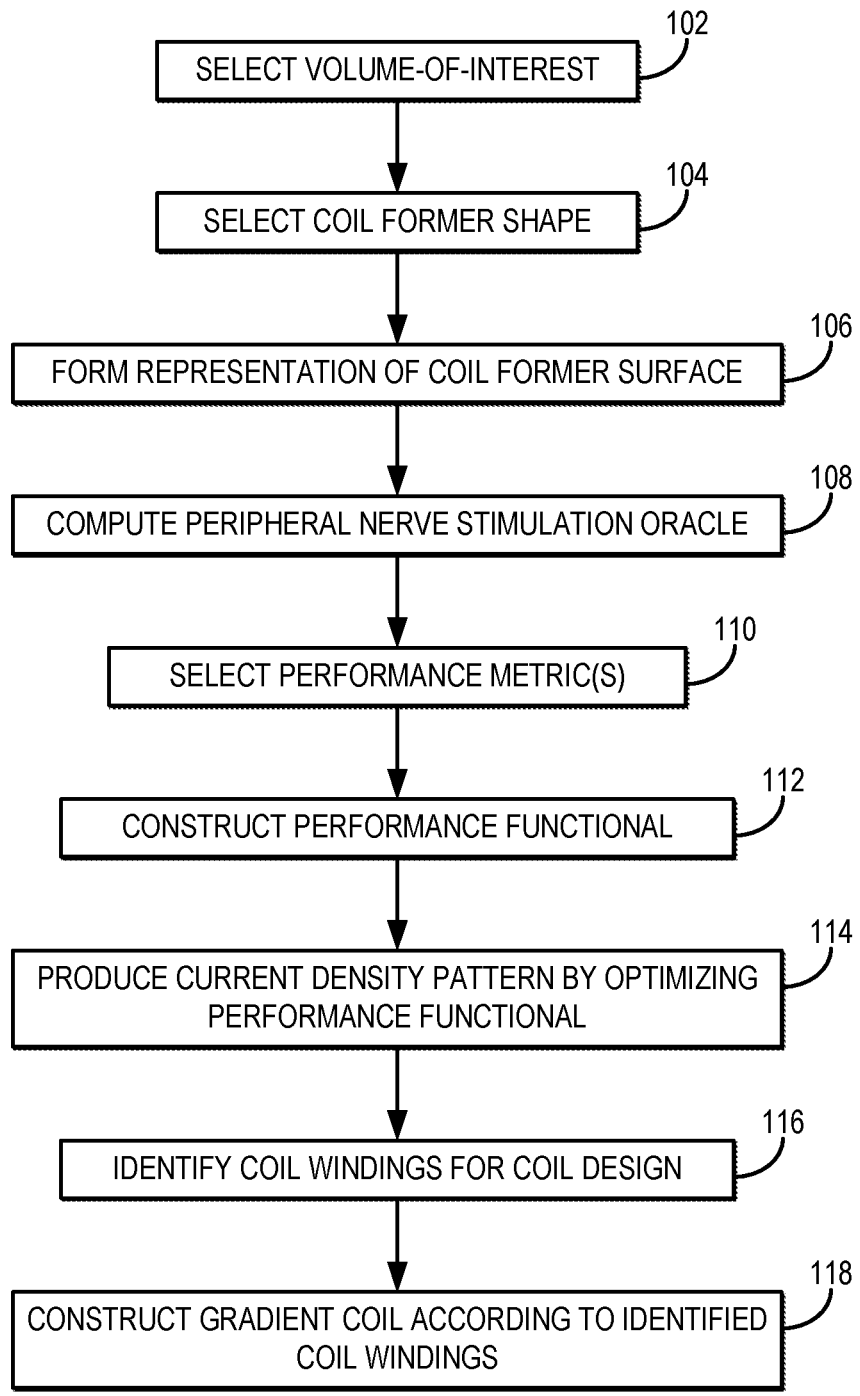
FIG. 1 is a flowchart setting forth the steps of an example method for designing an electromagnetic coil, such as a gradient coil, based on an oracle penalty method that implements an oracle computed for a peripheral nerve stimulation constraint on the coil design.

Described here are systems and methods for designing and manufacturing electromagnetic coils for use with a magnetic resonance imaging ("MRI") system. More particularly, described here are methods for designing and manufacturing gradient coils for producing magnetic field gradients with greater peripheral nerve stimulation ("PNS") thresholds relative to conventional gradient coils. In this way, magnetic field gradients can be generated with the designed gradient coils with significantly reduced likelihood of inducing PNS in a subject.

As one example, gradient coils can be designed with at least two-fold greater PNS thresholds than currently available gradient coils at acceptable cost in terms of other performance metrics, such as gradient linearity and inductance. These PNS-optimized coils can, therefore, be driven twice as fast as conventional coils without inducing PNS. Advantageously, the gradient coils designed using the methods described in the present disclosure may result in shorter ramp time of the gradient waveforms relative to conventional gradient coils, which can result in reduce echo-time, faster imaging, and reduced image distortions.

When gradient coils are designed and constructed, certain performance metrics can be considered. Examples of performance metrics that can be considered when designing and constructing a gradient coil include the net force experienced by the gradient coil when it is energized, the net torque experience by the gradient coil when it is energized, the efficiency of the gradient coil, the power dissipation of the gradient coil, the energy of the gradient coil, the shape of the magnetic field generated by the gradient coil, metrics related to eddy-current induced fields, and so on.

As described in the present disclosure, these performance metrics can be considered in addition to one or more PNS metrics that explicitly account for the effect the gradient coil design will have on inducing PNS. In general, the methods for designing gradient coils include using an optimization with one or more explicit constraints for PNS, which may be implemented using an oracle optimization method in which an oracle parameter is generated to constrain PNS.

As one example, a PNS oracle is generated to allow for the ultra-fast prediction of the propensity for magnetic field gradients generated by a gradient coil design to create an action potential in a subject, which is the physiological signature of onset PNS. The oracle can be pre-calculated based on a detailed calibrated model of the neurodynamic responses of nerve fibers to arbitrary external electric fields. This PNS oracle allows for highly accurate prediction of PNS onset and location without the need for a full neurodynamic simulation.

Using the methods described in the present disclosure, gradient coil designs can span a very large space of possible tradeoffs between a number of performance metrics, such as a gradient linearity metric, engineering metrics (e.g., power dissipation, torque, inductance), and an explicit PNS metric. For instance, the PNS-optimized coil design techniques described in the present disclosure allow for continuously trading off field linearity, power dissipation, inductance, torque, other performance metrics, and PNS. Depending on the application, the coil designer can choose the weights of the different tradeoffs and, therefore, design the best possible coil for the intended application with full consideration of PNS. This new design tool has access to regions of the performance metric/PNS metric tradeoff space that are not otherwise accessible.

The methods described in the present disclosure can be used to design any number of different gradient coil types, including body gradient coils, head gradient coils, or other anatomy specific gradient coils. Similarly, the methods can be used to design symmetrical or asymmetrical gradient coils. The methods can also be used to design other electromagnetic coils used in an MRI system, such as active shim coils. Further, when used in conjunction with a coil design technique such as boundary element method ("BEM"), the PNS-constrained design algorithm can be used to optimize wire patterns on arbitrary surfaces. In other words, the coil former does not have to be cylindrical and can even contain holes. This gives tremendous flexibility to coil designers.

Additionally or alternatively, the methods described in the present disclosure can be used to enhance and target electromagnetic stimulation provided to a subject, such as in a nerve stimulation device. This result can be achieved by including the PNS oracle in an optimization procedure for the driving weights of external coils and/or electrode arrays. The arrays are placed around the body part of interest (e.g., the pelvis when targeting the sciatic nerve) and are driven with the currents and/or voltages optimized with the PNS oracle. Such a method is applicable to both coil arrays (e.g., magnetostimulation) and electromagnetic stimulation with electrodes. In this way, electromagnetic stimulation devices can be optimized for a number of different applications. For instance, an electromagnetic stimulation device could be optimized for applications such as occipital nerve stimulation for the treatment of migraines, pudendal nerve stimulation for the treatment of urinary bladder incontinence, and sciatic nerve stimulation for the treatment of back pain.

The PNS oracle can be used for optimization of the voltages and/or currents imposed to an existing electromagnetic device, or to design the electromagnetic device itself. In the first case, the electromagnetic coil arrangement is given or fixed, and the current and voltage are optimized using the PNS oracle in order to maximize stimulation of the peripheral nerve target. In the second case, the PNS oracle is used to design the arrangement of coil windings or electrodes in two or three dimensions for the same effect.

Thus, the systems and methods described in the present disclosure provide for the design of electromagnetic coils, which may be gradient coils for use in an MRI system or electrodes or electrode arrays or coil winding patterns for use with electromagnetic stimulation systems, with an intrinsic capability to control PNS, either to reduce PNS in MRI or create it in pain and other electromagnetic stimulation treatments. As will be described in more detail below, the systems and methods implement explicit PNS constraints in the design of the electromagnetic coils. The described framework allows for the prediction of PNS thresholds before having to construct an electromagnetic device prototype. In other words, an electromagnetic device can be designed and its characteristic PNS threshold computed using a computer system before actually building the device. In other words, the PNS oracle and the PNS simulation allow computational prototyping of the electromagnetic device.

As will be described, an explicit PNS constraint can be implemented using an oracle penalty method, in which the oracle parameter is computed based on PNS reference data, which may in some instances include PNS simulation data. The PNS oracle can be created, for example, using a full PNS simulation approach.

In general, the PNS oracle describes the relationship between a PNS threshold and the applied current to general wire elements, from which any wire pattern can be built. By monitoring the sum of these linear contributions during the wire-pattern optimization process, the amount of expected, predicted, or otherwise estimated PNS can be continuously monitored and constrained in the design process, similar to how other undesirable aspects of the winding pattern (e.g., inductance and gradient production inefficiency) can be constrained. The PNS oracle is considerably simpler than a full simulation of the nerve dynamics, in that the PNS oracle pre-computes the response of many small nerve segments with various diameters using, as an input, the electric field variation along those nerve paths.

The linear and pre-computed nature of the oracle makes it a very fast predictor of PNS occurrence for a complex wire pattern, which makes it well-adapted to the problem of fast optimization of coil and electrode configurations. As described above, the PNS oracle can be used both to optimize gradient coil windings for MRI, in which PNS sensation needs to be reduced, and coil and electrode array arrangements for the treatment of pain or other electromagnetic stimulation applications in which PNS is created on purpose for nerve excitation or blocking.

For the gradient coil design application, PNS reduction is achieved by incorporating the PNS oracle into the coil winding optimization algorithm, which may be a BEM-based coil design algorithm. In this approach, the gradient coil wire pattern (e.g., coil windings) is optimized so as to create a linear magnetic field distribution (i.e., a magnetic field gradient) in the field-of-view of the scanner, to use a minimum amount of energy, and to have good engineering properties (e.g., minimal torque, forces, power dissipation). The PNS oracle is additionally used in the BEM method so as to obtain gradient coil designs that have improved PNS characteristics in addition to the good imaging and engineering performances. As a result, the PNS-constrained coil designs can be driven at greater speed and power without inducing PNS, which has a beneficial impact on acquisition speed and image quality.

Although BEM is described as an example method for implementing the coil design process, the systems and methods described in the present disclosure can alternatively be implemented with other optimization algorithms to design the electromagnetic coil. That is, the PNS constraints in the form of a fast oracle within an optimization procedure to reduce PNS can be implemented in coil design techniques other than a BEM-based approach.

For the electromagnetic stimulation application, the PNS oracle can be used to quickly optimize driving patterns of coil and electrode arrays placed around the body part of interest. This can be achieved by applying currents (coil arrays) and voltages (electrode arrays) in a strategic manner so as to selectively excite the targeted nerve segments (or group of nerve segments). These specifically tailored current and voltage distributions can be computed using an optimization procedure using the PNS oracle in order to produce in vivo field patterns that stimulate the targeted nerves while being sub-threshold for other nerves, such that the other nerves do not experience stimulation.

To achieve the performance metric limits associated with different performance metric requirements, a representation of the current density for the gradient coils over the surface where the gradient coils are to reside (e.g., a cylindrical coil former or other shaped coil former) can be generated. This representation can be analytic, usually incorporating some sort of basis representation for the given geometry. For example, where the gradient coils are to reside on a cylinder, cylindrical harmonics can be used as the basis representation. Alternatively, the representation can be numerical. For example, the current density for the gradient coils can be based on current elements over a finite triangular mesh.

In a BEM-based approach to coil design, any surface on which electrical current can flow can be approximated or represented by a collection of elements (e.g., triangular elements) that form a mesh over the whole surface. The vertices of the elements in the mesh are referred to as nodes. Within each element is contained information that describes the direction and magnitude of the electrical current density. Thus, to design a gradient coil using BEM-based techniques, a surface geometry is discretized into a finite mesh composed of finite elements, which as noted may be triangular elements or other shaped elements.

In practice, the current density pattern over a two dimensional surface can be represented in an indirect manner in the form of a scalar stream function. The stream function can be represented as a piece-wise linear (or higher order) function over the surface geometry on which the gradient coils are to be placed. The stream function can include a single scalar value for each node in the mesh, and when all of the nodes are considered together, the stream function can be transformed to find the direction and magnitude of the current density in each element.

The current density representation, or the stream functions, can be used to produce a pattern of current density that achieves the set requirements for the PNS metric and one or more performance metrics. As one non-limiting example, the current density representation, or the stream functions, can be used to produce a pattern of current density that balances achieving a target magnetic field within the PNS constraints defined by the PNS oracle parameter, while at the same time satisfying specified requirements for net torque, net force, power dissipation, or combinations thereof.

As mentioned above, the systems and methods described in the present disclosure implement an oracle penalty method to provide for an explicit constraint on PNS during the design of an electromagnetic coil, such as a gradient coil for use with an MRI system. The coil design process can implement a constrained optimization problem, which in general can be defined as, $$\min f(x); \qquad (1)$$

subject to one or more constraints, $g_i(x)$, which may be equality constraints, inequality constraints, or combinations thereof. When implementing an oracle penalty, the objective function, $f(x)$, is transformed into an additional equality constraint:

$$g_0(x) = f(x) - \Omega = 0, \Omega \in \mathbb{R}; \qquad (2)$$

where $\Omega$ is a parameter referred to as the oracle. The transformed objective function problem can then be restated as:

$$\min \tilde{f}(x) \equiv 0$$

Subject to the oracle constraint, $g_0(x)$, and one or more additional constraints, $g_i(x)$, which may be equality constraints, inequality constraints, or combinations thereof.

In some instances, the oracle constraint can be implemented as a penalty function, such as the following penalty function:

$$p(x) = \alpha \cdot |f(x) - \Omega| + (1 - \alpha) \cdot res(x); \qquad (3)$$

Where $res(x)$ is the residual of the original constraints, $g_i(x)$, and $\alpha$ is a penalty weight that balances between the transformed objective function and the original constraints, and which may be given by:

$$\alpha = \begin{cases} 1 - \dfrac{1}{2\sqrt{\dfrac{|f(x) - \Omega|}{r(x)}}}, & \text{if } res(x) \le |f(x) - \Omega| \\ \dfrac{1}{2}\sqrt{\dfrac{|f(x) - \Omega|}{r(x)}}, & \text{if } res(x) > |f(x) - \Omega| \end{cases} \qquad (4)$$

In general, the penalty weight will take a value between zero and one, where values between 0 and 0.5 focus the weight on the residual and values between 0.5 and 1 focus the weight on the transformed objective function. Additional examples of oracle penalty functions and implementations of an oracle constrained optimization are described by M. Schluter and M. Gerdts in "The Oracle Penalty Method," *Journal of Global Optimization*, 2010; 47(2):293-325, which is herein incorporated by reference in its entirety.

Referring now to FIG. 1, a flowchart is illustrated as setting forth the steps of an example of a method for designing, and constructing, an electromagnetic coil (e.g., a gradient coil) for use with an MRI system.

The method includes selecting a volume-of-interest in which the magnetic field gradient will be generated, as indicated at step 102. As one example, the volume-of-interest is selected to correspond with a volume within the main magnetic field of the MRI system for which the gradient coil is being designed, or other similar MRI systems.

The shape of the surface on which the gradient coil will be constructed is next selected, as indicated at step 104. As one example, the shape of this surface may be a cylinder within the bore of the MRI system for which the gradient coil is being designed, or other similar MRI systems. In other examples, shapes other than cylinders may be used, including arbitrary shapes that are selected or otherwise designed to conform to, or be sized to receive, a particular anatomical region.

One or more representations of the selected surface are then formed, as indicated at step 106. As described above, this step can include forming a mesh representation of the selected surface. As one example, the mesh can include a triangulated mesh that is composed of elements, which may be triangular elements.

A PNS oracle is computed based on reference PNS data, as indicated at step 108. For instance, the PNS oracle can be computed from the electric potential changes along the nerve segments. These potential changes can be obtained from the simulated electric fields that are induced either by switching of the coil, coil segments, or electrical current basis elements, or by direct application of electric fields using electrodes. In some implementations, the PNS oracle computation only uses linear operations; namely, projection of the electric field onto the nerve paths, integration to obtain electric potentials, differentiation, convolution, and scaling. The convolution kernel and the scaling parameter can be calibrated based on reference thresholds obtained from full neurodynamic models to ensure that the PNS oracle accurately predicts these reference thresholds. All operations used for calculating the PNS oracle can be linear, which ensures that the PNS oracle is linear in the induced electric fields (and thus the applied coil currents or electrode voltages). One or more performance metrics for the design of the coil are also selected and set, as indicated at step 110.

For example, a gradient coil is typically designed and constructed so as to reduce the net force and the net torque experienced by the gradient coil when energized. Net force can be characterized in each of the x, y, and z directions in terms of Newtons per Ampere of current ("N/A"). This quantity determines the tendency for the gradient coil to translate in space when energized. Net torque can be characterized in each of the x, y, and z directions in terms of Newtons per meter per Ampere ("N/m/A"). This quantity determines the tendency for the gradient coil to rotate when energized. The reduction in the net force and the net torque experienced by a gradient coil is made in consideration of other performance metrics, limits, or requirements. Thus, in some implementations, optimum force-balance and torque-balance may be sacrificed to achieve requirements set for the PNS metric and other performance metrics.

Efficiency is another performance metric that can be considered when constructing gradient coils. Efficiency can be defined as the gradient strength per unit current driven through the gradient coils. High efficiency aids the production of large gradient amplitudes, which in turn can allow the acquisition of higher resolution images or reduce scan times. Efficiency is linearly proportional to the winding density of the gradient coils. For example, when the winding density is doubled, the efficiency typically doubles as well. Accordingly, gradient coils are typically constructed with as high an efficiency as possible, in light of other performance metrics, including requirements set for other performance metrics. Thus, in some implementations, optimum efficiency may be sacrificed to achieve requirements set for other performance metrics. For example, a particular winding density can be chosen to obtain a desired efficiency that may be lower than the highest possible efficiency so that limits for the PNS metric and other performance metrics can be met.

Power dissipation is yet another performance metric that can be considered. Power dissipation can be determined based on power, which is the resistance of the gradient coils multiplied by the current squared. Accordingly, power dissipation can be a measure of the amount of heat that can be created when the gradient coils are energized. Power dissipation is proportional to the square of the winding density. For example, when the winding density is doubled, the power dissipation typically quadruples. Accordingly, gradient coils can be constructed with as low a power dissipation (and thus heat generation) as possible, in light of the PNS metric and other performance metric requirements set. For example, a particular winding density can be chosen to obtain a desired power dissipation that may be higher than the lowest possible power dissipation so that set requirements for the PNS metric and other performance metrics can be met.

Energy is yet another performance metric that can be considered when constructing gradient coils. Energy can be defined as one-half of the inductance of the gradient coils multiplied by the current squared. This metric can be a measure of how fast the gradient coils can be switched on or off. Lower energy typically implies faster switching rates. Energy, similar to power dissipation, is proportional with the square of the winding density. For example, when the winding density is doubled, the energy typically quadruples. Accordingly, gradient coils can be constructed with the lowest energy (and thus fastest switching) as possible, in light of the PNS metric and other performance metric requirements. For example, a particular winding density can be chosen to obtain a desired energy that may be higher than the lowest possible energy so that the requirements set for the PNS metric and other performance metrics can be met.

Gradient field-shape is yet another performance metric that can be considered when constructing gradient coils. Magnetic field gradient linearity and uniformity is typically a primary consideration when implementing gradient coils. Gradient field-shape is a measure of how well the magnetic field produced by a gradient coil matches a target gradient field. There are many ways that this gradient field-shape metric can be defined. As one example, the gradient field-shape metric can be defined as the sum of the squared difference between the field that is produced by the gradient coils and the target gradient field over a set of positions in a volume-of-interest. Based on this definition, the gradient field-shape metric is lowered, to the extent possible, in light of the PNS metric and other performance metric requirements specified. For example, a particular winding pattern can be chosen to obtain a particular gradient linearity metric that may be higher than the lowest possible gradient linearity metric so that specified requirements for the PNS metric and other performance metrics can be met.

Other performance metrics known to persons having ordinary skill in the art of magnetic resonance imaging, such as those related to eddy current-induced fields and other metrics, can also be defined and considered when constructing gradient coils.

Referring still to FIG. 1, to find the stream function and corresponding current density representation that achieves the specified requirements set for the gradient coil design, a performance functional is formed based at least in part on the set performance metrics and the PNS oracle, as indicated at step 112. The performance functional can be, for instance, a cost function including one or more terms associated with the performance metrics and a penalty function and/or constraint associated with and incorporating the PNS oracle. In some implementations, the performance metrics can be implemented in the performance functional as weighting parameters. In other implementations, the performance metrics can be implemented in the performance functional as constraints set on the performance functional. A constraint can be set in the form of a single value (i.e., constrained to zero) or a range of values that are acceptable for that performance metric. The approaches for implementing the performance metrics can also be combined. For instance, some performance metrics can be used to constrain the performance functional and other performance metrics can be implemented as weighting parameters in the performance functional.

Once the performance functional is formed, it can be minimized or optimized to produce a current density pattern that achieves the specified gradient coil performance metric constraints, as indicated at step 114. The minimization can be based on various techniques such as least-squares matrix inversion, analytic formulas, or an iterative solver.

For example, where one or more performance metrics are set as weighting parameters, competing performance metrics can be simultaneously balanced to achieve the desired PNS metric (e.g., reduced propensity to induce PNS) and performance metric requirements (e.g., low power dissipation, low net force, low net torque) by finding a set of parameters that minimizes the performance functional. As another example, where one or more performance metrics are set as constraints, a constrained optimization can be used to find the desired performance metric requirements in addition to the PNS metric defined by the PNS oracle.

In some implementations, the solution of the performance functional itself can be constrained to a certain desired range. If the solution is not within this desired range, then performance metrics or weighting parameters can be changed, for example, to obtain a different solution. This process can be iteratively repeated until the solution is within the range of acceptable design goals. Example design goals include minimum conductor separation, maximum power deposition per unit area, maximum force on a given component, and so on.

Coil windings for the gradient coil are then identified based on the minimized performance functional, as indicated at step 116. For instance, current density can be computed based on the minimized performance functional and coil windings can be determined based on the computed current density. As an example, the current density pattern obtained by minimizing or optimizing the performance functional can be contoured to obtain a wire pattern, which is a discrete number of current paths that approximates the current density represented by the stream function. The choice of number of contours (and thus the coil wire density) can also be based on the performance metric weightings and constraints since some of the performance metric weightings and constraints may be related to wire density (e.g., a constraint to enforce a certain minimum wire separation). Using the identified coil windings, a gradient coil can then be constructed, as indicated at step 118.

Figure 2:
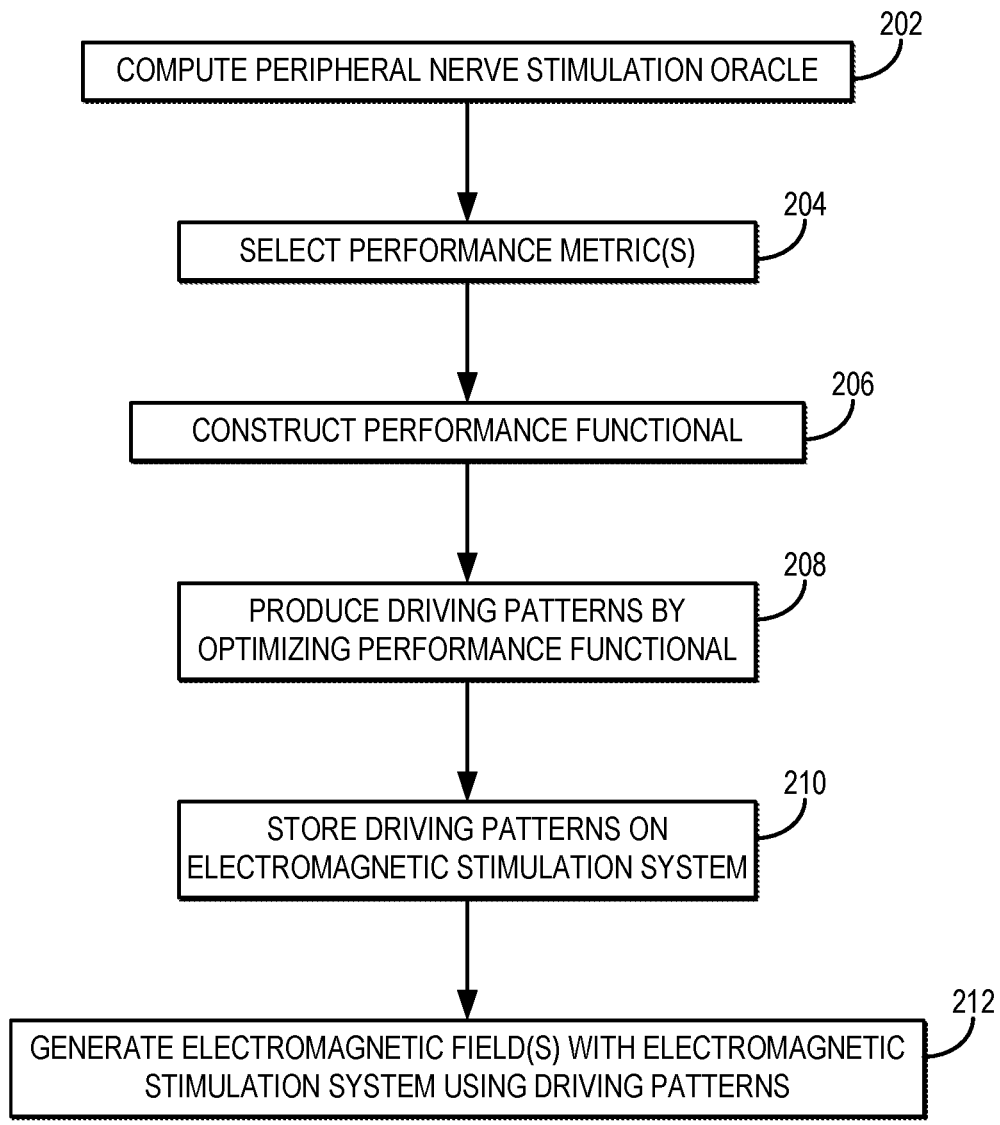
FIG. 2 is a flowchart setting forth the steps of an example method for controlling the operation of an electromagnetic stimulation system based on an optimized driving pattern generated using an oracle penalty method that implements an oracle computed for a peripheral nerve stimulation constraint on the driving pattern optimization.

Referring now to FIG. 2, a flowchart is illustrated as setting forth the steps of an example of a method for controlling the operation of an electromagnetic stimulation system to generate electromagnetic fields that are tailored to excite or block nerve stimulation.

The method includes computing a PNS oracle based on reference PNS data, as indicated at step 202. For instance, a PNS oracle parameter can be computed based on a full PNS simulation, such that the reference PNS data are simulation data. In such examples, the PNS oracle parameter can be computed based on a detailed calibrated model of the neurodynamic responses of nerve fibers to arbitrary external electric fields. One or more additional performance metrics are also selected, as indicated at step 204. These performance metrics may be constraints, weights, or both, that represent desired and/or undesired performance characteristics of the electromagnetic stimulation system.

An objective function that represents a performance functional for the electromagnetic stimulation system is then constructed using the PNS oracle and the one or more performance metrics, as indicated at step 206. The objective function represents a constrained optimization problem, which is solved, generating output as optimized driving patterns for the electrode(s), electrode array(s), and/or coil (s) of the electromagnetic stimulation system, as indicated at step 208. These optimized driving patterns are thus stored for use by the electromagnetic stimulation system, as indicated at step 210. The optimized driving patterns can then be used by the electromagnetic stimulation system to generate electromagnetic fields that result in the desired nerve excitation, nerve blocking, or both, as indicated at step 212. For instance, the optimized driving patterns can be retrieved by the electromagnetic stimulation system and used to apply currents and/or voltages so as to selectively excite the targeted nerve segments (or group of nerve segments).

The objective can be an optimization of the driving pattern of an existing electromagnetic device, or an optimization of the electromagnetic device itself. In this case, the geometry of the electromagnetic device is being establish by minimization of the objective functional, of which the PNS oracle is a component.

Figure 3:
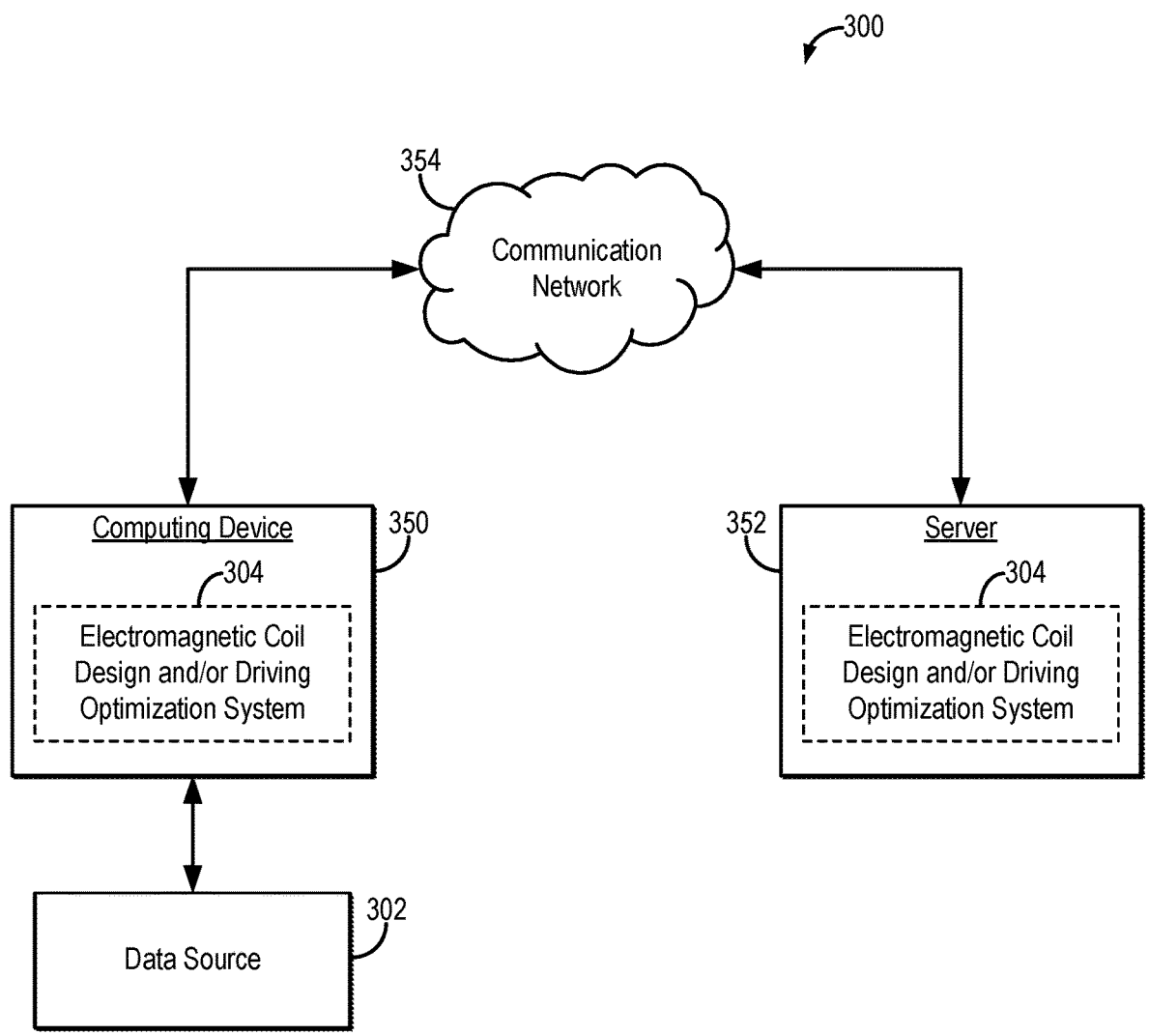
FIG. 3 is a block diagram of an example system for designing an electromagnetic coil and/or optimizing a driving pattern for an electromagnetic stimulation system.

Referring now to FIG. 3, an example of a system 300 for designing and or optimizing the control of electromagnetic coils for use in MRI and/or electromagnetic stimulation in accordance with some embodiments of the systems and methods described in the present disclosure is shown. As shown in FIG. 3, a computing device 350 can receive one or more types of data (e.g., reference PNS data) from data source 302. In some embodiments, computing device 350 can execute at least a portion of a electromagnetic coil design and/or driving optimization system 304 to design electromagnetic coils and/or determine optimized driving patterns for such coils.

Additionally or alternatively, in some embodiments, the computing device 350 can communicate information about data received from the data source 302 to a server 352 over a communication network 354, which can execute at least a portion of the electromagnetic coil design and/or driving optimization system 304. In such embodiments, the server 352 can return information to the computing device 350 (and/or any other suitable computing device) indicative of an output of the electromagnetic coil design and/or driving optimization system 304.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, data source 302 can be any suitable source of data (e.g., measurement data, reference or simulation peripheral nerve stimulation data), another computing device (e.g., a server storing image data), and so on. In some embodiments, data source 302 can be local to computing device 350. For example, data source 302 can be incorporated with computing device 350 (e.g., computing device 350 can be configured as part of a device for capturing, scanning, and/or storing images). As another example, data source 302 can be connected to computing device 350 by a cable, a direct wireless link, and so on. Additionally or alternatively, in some embodiments, data source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 354 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
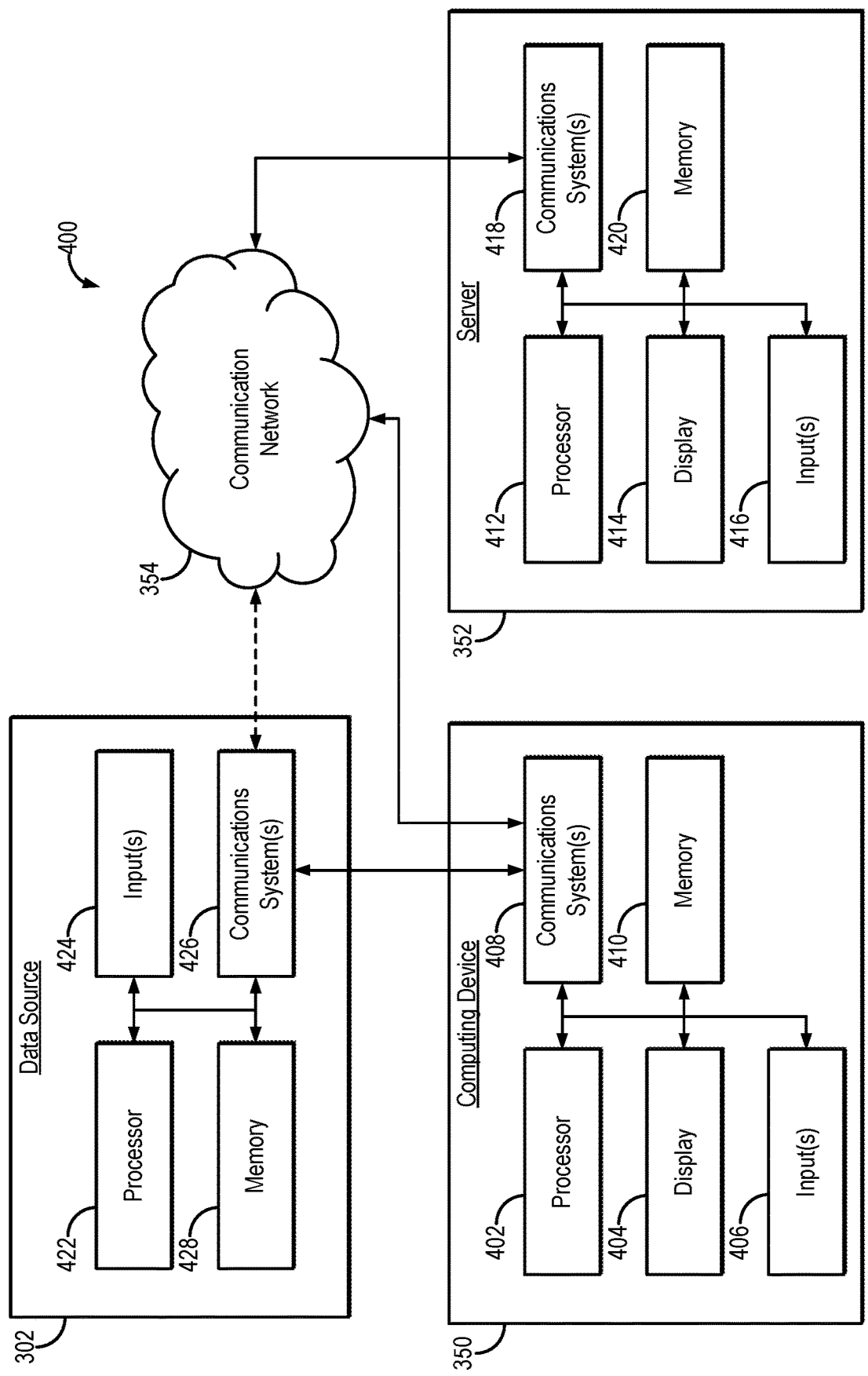
FIG. 4 is a block diagram of example components that can implement the system of FIG. 3.

Referring now to FIG. 4, an example of hardware 400 that can be used to implement data source 302, computing device 350, and server 352 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, data source 302 can include a processor 422, one or more inputs 424, one or more communications systems 426, and/or memory 428. In some embodiments, processor 422 can be any suitable hardware processor or combination of processors, such as a CPU, a GPU, and so on. In some embodiments, the one or more input(s) 424 are generally configured to receive data, such as reference PNS data and other associated data for use in designing electromagnetic coils and/or optimizing the driving patterns for such coils. Additionally or alternatively, in some embodiments, one or more input(s) 424 can include any suitable hardware, firmware, and/or software for coupling to and/or controlling operations of a system for simulating PNS data. In some embodiments, one or more portions of the one or more input(s) 424 can be removable and/or replaceable.

Note that, although not shown, data source 302 can include any suitable inputs and/or outputs. For example, data source 302 can include input devices and/or sensors that can be used to receive user input, such as a keyboard, a mouse, a touchscreen, a microphone, a trackpad, a trackball, and so on. As another example, data source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more input(s) 424, and/or receive data from the one or more input(s) 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of data source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 5:
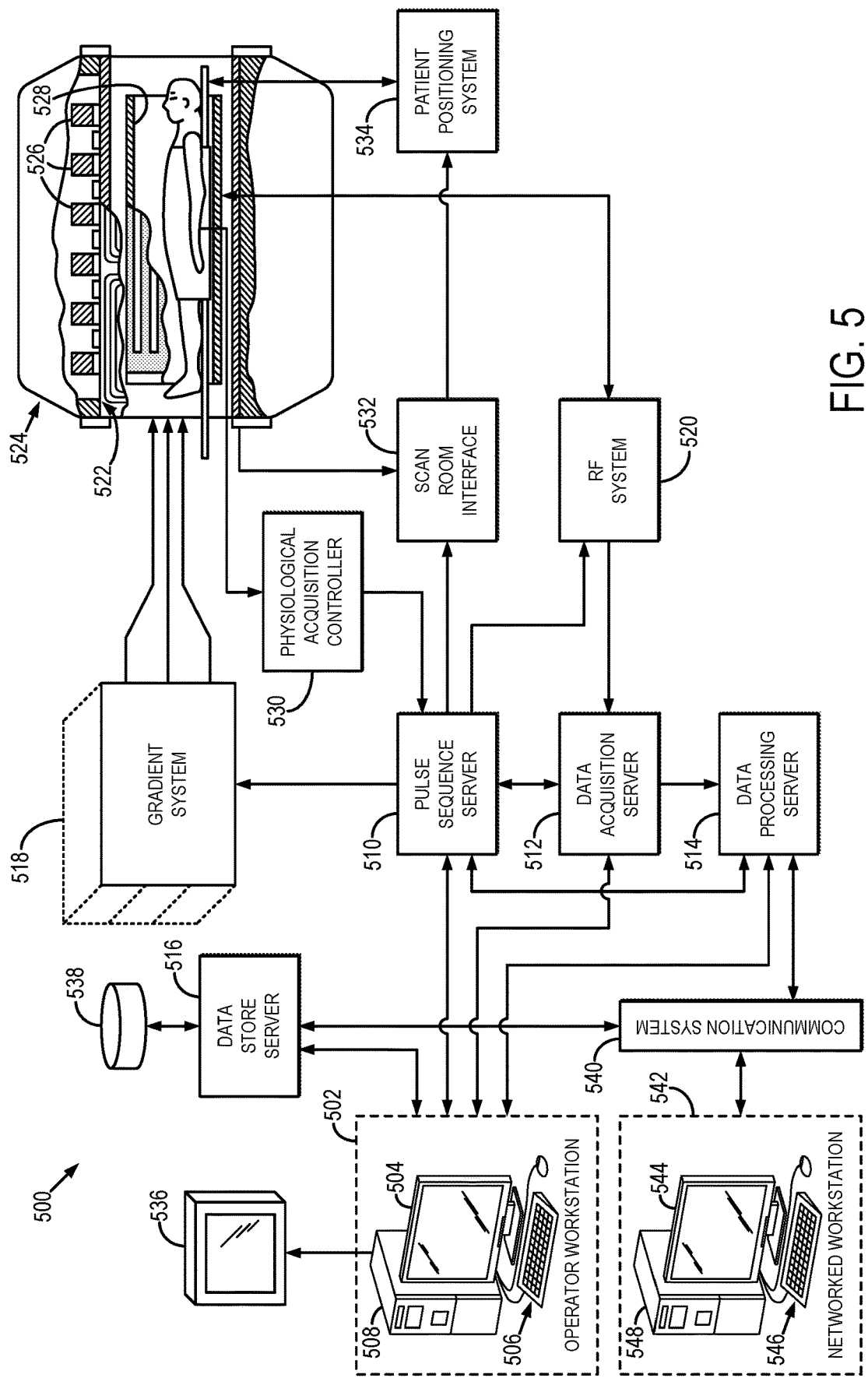
FIG. 5 is a block diagram of an example magnetic resonance imaging (MRI) system that can implement the methods described in the present disclosure.

Referring particularly now to FIG. 5, an example of an MRI system 500 that can implement the methods described here is illustrated. The MRI system 500 includes an operator workstation 502 that may include a display 504, one or more input devices 506 (e.g., a keyboard, a mouse), and a processor 508. The processor 508 may include a commercially available programmable machine running a commercially available operating system. The operator workstation 502 provides an operator interface that facilitates entering scan parameters into the MRI system 500. The operator workstation 502 may be coupled to different servers, including, for example, a pulse sequence server 510, a data acquisition server 512, a data processing server 514, and a data store server 516. The operator workstation 502 and the servers 510, 512, 514, and 516 may be connected via a communication system 540, which may include wired or wireless network connections.

The pulse sequence server 510 functions in response to instructions provided by the operator workstation 502 to operate a gradient system 518 and a radiofrequency ("RF") system 520. Gradient waveforms for performing a prescribed scan are produced and applied to the gradient system 518, which then excites gradient coils in an assembly 522 to produce the magnetic field gradients $G_x$, $G_y$, and $G_z$ that are used for spatially encoding magnetic resonance signals. The gradient coil assembly 522 forms part of a magnet assembly 524 that includes a polarizing magnet 526 and a whole-body RF coil 528.

RF waveforms are applied by the RF system 520 to the RF coil 528, or a separate local coil to perform the prescribed magnetic resonance pulse sequence. Responsive magnetic resonance signals detected by the RF coil 528, or a separate local coil, are received by the RF system 520. The responsive magnetic resonance signals may be amplified, demodulated, filtered, and digitized under direction of commands produced by the pulse sequence server 510. The RF system 520 includes an RF transmitter for producing a wide variety of RF pulses used in MRI pulse sequences. The RF transmitter is responsive to the prescribed scan and direction from the pulse sequence server 510 to produce RF pulses of the desired frequency, phase, and pulse amplitude waveform. The generated RF pulses may be applied to the whole-body RF coil 528 or to one or more local coils or coil arrays.

The RF system 520 also includes one or more RF receiver channels. An RF receiver channel includes an RF preamplifier that amplifies the magnetic resonance signal received by the coil 528 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} ; \tag{5}$$

and the phase of the received magnetic resonance signal may also be determined according to the following relationship:

$$\varphi = \tan^{-1}\left(\frac{Q}{I}\right). \tag{6}$$

The pulse sequence server 510 may receive patient data from a physiological acquisition controller 530. By way of example, the physiological acquisition controller 530 may receive signals from a number of different sensors connected to the patient, including electrocardiograph ("ECG") signals from electrodes, or respiratory signals from a respiratory bellows or other respiratory monitoring devices. These signals may be used by the pulse sequence server 510 to synchronize, or "gate," the performance of the scan with the subject's heart beat or respiration.

The pulse sequence server 510 may also connect to a scan room interface circuit 532 that receives signals from various sensors associated with the condition of the patient and the magnet system. Through the scan room interface circuit 532, a patient positioning system 534 can receive commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, so that data is not lost by data overrun. In some scans, the data acquisition server 512 passes the acquired magnetic resonance data to the data processor server 514. In scans that require information derived from acquired magnetic resonance data to control the further performance of the scan, the data acquisition server 512 may be programmed to produce such information and convey it to the pulse sequence server 510. For example, during pre-scans, magnetic resonance data may be acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also process magnetic resonance signals used to detect the arrival of a contrast agent in a magnetic resonance angiography ("MRA") scan. For example, the data acquisition server 512 may acquire magnetic resonance data and processes it in real-time to produce information that is used to control the scan.

The data processing server 514 receives magnetic resonance data from the data acquisition server 512 and processes the magnetic resonance data in accordance with instructions provided by the operator workstation 502. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 514 are conveyed back to the operator workstation 502 for storage. Real-time images may be stored in a data base memory cache, from which they may be output to operator display 502 or a display 536. Batch mode images or selected real time images may be stored in a host database on disc storage 538. When such images have been reconstructed and transferred to storage, the data processing server 514 may notify the data store server 516 on the operator workstation 502. The operator workstation 502 may be used by an operator to archive the images, produce films, or send the images via a network to other facilities.

The MRI system 500 may also include one or more networked workstations 542. For example, a networked workstation 542 may include a display 544, one or more input devices 546 (e.g., a keyboard, a mouse), and a processor 548. The networked workstation 542 may be located within the same facility as the operator workstation 502, or in a different facility, such as a different healthcare institution or clinic.

The networked workstation 542 may gain remote access to the data processing server 514 or data store server 516 via the communication system 540. Accordingly, multiple networked workstations 542 may have access to the data processing server 514 and the data store server 516. In this manner, magnetic resonance data, reconstructed images, or other data may be exchanged between the data processing server 514 or the data store server 516 and the networked workstations 542, such that the data or images may be remotely processed by a networked workstation 542.

Figure 6:
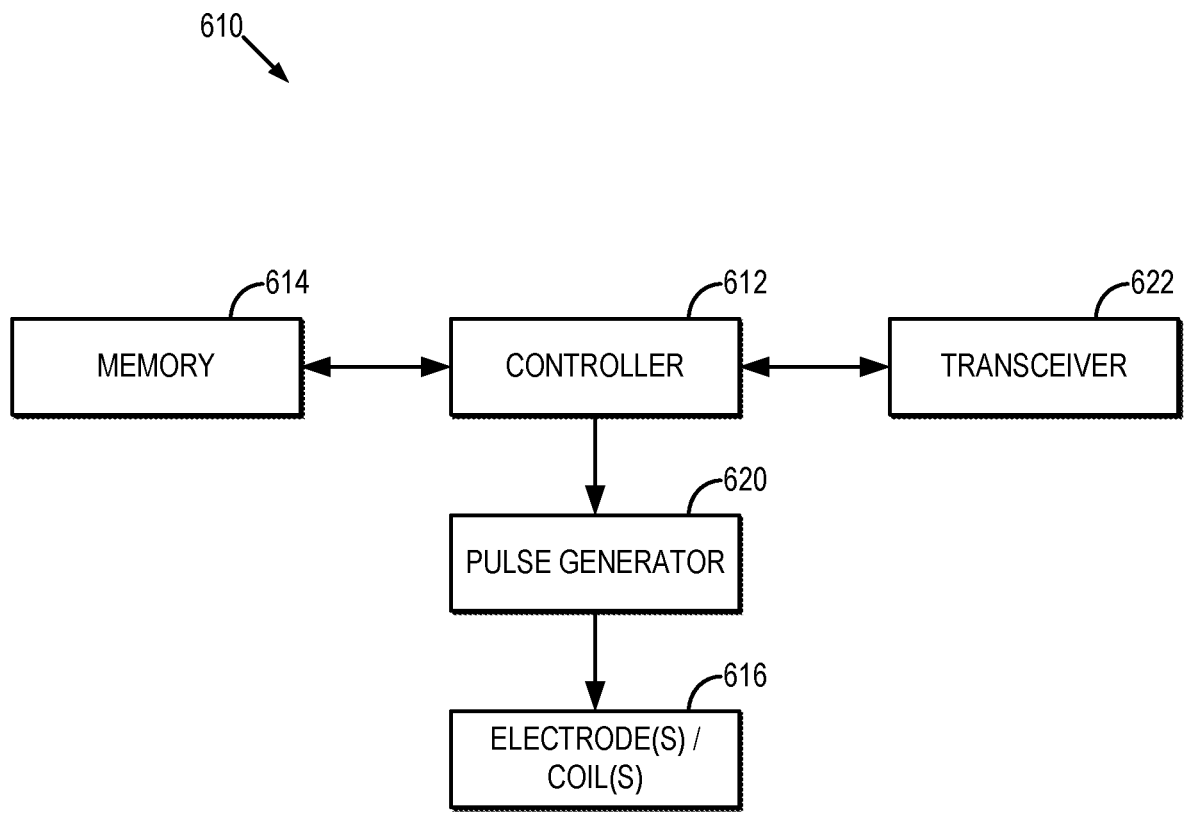
FIG. 6 is a block diagram of an example electromagnetic stimulation system that can implement the methods described in the present disclosure.

Referring now to FIG. 6, an example electromagnetic stimulation system 610 that can implement the methods described above is illustrated. In general, the electromagnetic stimulation system 610 includes a controller 612, a memory 614, and at least one electrode 616, which may be a single electrode or an electrode array (e.g., as may be used in magnetostimulation systems), and/or wire windings (e.g., coils). The electromagnetic stimulation system 610 can be implemented as an externally applied medical device (e.g., a surface electrode) or as an implantable medical device (e.g., such as an implanted neuromodulation system).

In some embodiments, at least one electrode 616 is capable of both sensing electrophysiological activity and delivering electromagnetic stimulation. Thus, in these embodiments, the at least one electrode 616 also forms at least one sensor.

The controller 612 includes a processor to execute instructions embedded in or otherwise stored on the memory 614 to implement the methods described above. The memory 614 can also store settings (e.g., driving patterns, stimulation parameters) to be provided to the controller 612 for directing the at least one electrode 616 to provide electromagnetic stimulation to a subject.

At least one electrode or coil 616 operates under control of the controller 612 to deliver electromagnetic stimulations to the subject in response thereto. Processing circuitry in the controller 612 determines the optimized stimulation parameters based on the methods and algorithms described above. The optimized stimulation parameters are provided as instructions to a pulse generator 620, which in response to the instructions provides an electrical signal to the at least one electrode or coil 616 to deliver the electromagnetic stimulations to the subject.

The electromagnetic stimulation system 610 can also include a transceiver 622 and associated circuitry for communicating with a programmer or other external or internal device. As one example, the transceiver 622 can include a telemetry coil.

In operation, the electromagnetic stimulation system 610 receives, or computes via the controller 612, optimal stimulation parameters (e.g., driving patterns), as described above. The optimized stimulation parameters are provided to the pulse generator 620 to control the at least one electrode or coil 616 to generate electromagnetic stimulation that will achieve the desired effect in the subject.

The present disclosure has described one or more preferred embodiments, and it should be appreciated that many equivalents, alternatives, variations, and modifications, aside from those expressly stated, are possible and within the scope of the invention.

The invention claimed is:

1. A method of manufacturing an electromagnet coil for use in a magnetic resonance imaging (MRI) system, the method comprising:
   (a) computing a peripheral nerve stimulation (PNS) oracle penalty using a computer system, the PNS oracle penalty comprising a parameter representative of a PNS requirement for the electromagnetic coil;
   (b) setting a plurality of performance metric requirements for a plurality of performance metrics for the electromagnet coil using the computer system;
   (c) forming, by the computer system, a performance functional for generating a current density pattern over a coil surface for the electromagnetic coil, wherein the performance functional is based on the plurality of performance metrics and the PNS oracle penalty;

(d) optimizing, by the computer system, the performance functional based on the PNS requirement and the plurality of performance metric requirements;

(e) generating, by the computer system, a current density pattern over the coil surface based on the optimized performance functional; and (f) outputting, to a display, information indicating the coil windings from the current density pattern.

2. A method for controlling the operation of an electromagnetic stimulation system, the method comprising:

(a) computing a peripheral nerve stimulation (PNS) oracle penalty using a computer system, the PNS oracle penalty comprising a parameter representative of a target nerve stimulation requirement for the electromagnetic stimulation system;

(b) setting a plurality of performance metric requirements for a plurality of performance metrics for the electromagnetic stimulation system using the computer system;

(c) forming, by the computer system, a performance functional for generating a stimulation driving pattern for the electromagnetic stimulation system, wherein the performance functional is based on the plurality of performance metrics and the PNS oracle penalty;

(d) optimizing, by the computer system, the performance functional based on the target nerve stimulation requirement and the plurality of performance metric requirements;

(e) generating, by the computer system, a stimulation driving pattern based on the optimized performance functional; and (f) storing the stimulation driving pattern to the electromagnetic stimulation system in order to generate an electromagnetic field that when applied to a subject causes the subject to receive nerve stimulation according to the target nerve stimulation requirement.

3. The method as recited in claim 1, wherein the PNS oracle penalty comprises a single oracle parameter.

4. The method as recited in claim 1, wherein the PNS oracle penalty comprises a penalty function that includes an oracle parameter.

5. The method as recited in claim 1, wherein the PNS oracle penalty is calibrated based on reference PNS data that describe neurodynamic responses of nerve fibers to arbitrary external electromagnetic fields.

6. The method as recited in claim 5, wherein the reference PNS data are simulation data generated based on a calibrated model of the neurodynamic responses of nerve fibers to arbitrary external electromagnetic fields.

7. The method as recited in claim 1, further comprising forming a coil representation of the coil surface for the electromagnet coil using the computer system, and wherein the performance functional is also based on the coil representation.

8. The method as recited in claim 7, wherein the coil representation is based on a boundary element method.

9. The method as recited in claim 1, wherein the plurality of performance metrics also include a magnetic field-shape metric.

10. The method as recited in claim 9, wherein the magnetic field-shape metric comprises a target magnetic field, and wherein optimizing the performance functional further comprises optimizing a difference between the target magnetic field and a predicted magnetic field generated based on the performance functional.

11. The method as recited in claim 1, wherein the current density pattern is based on a stream function.

12. The method as recited in claim 1, wherein the plurality of performance metrics further comprise at least one of a net force metric, a net torque metric, a field homogeneity metric, a dissipative power metric, or an energy metric.

13. The method as recited in claim 1, wherein the coil surface is cylindrical.

14. The method as recited in claim 1, wherein the electromagnetic coil is a gradient coil.

15. The method as recited in claim 14, wherein the gradient coil is an asymmetric gradient coil that generates a magnetic field having a magnet center that is offset from a geometric center of the gradient coil.

16. The method as recited in claim 1, wherein the electromagnetic coil comprises at least one of a winding pattern or an electrode configuration for use with an electromagnetic stimulation device.

17. The method as recited in claim 2, wherein the PNS oracle penalty comprises a single oracle parameter.

18. The method as recited in claim 2, wherein the PNS oracle penalty comprises a penalty function that includes an oracle parameter.

19. The method as recited in claim 2, wherein the PNS oracle penalty is computed from reference PNS data that describe neurodynamic responses of nerve fibers to arbitrary external electromagnetic fields.

20. The method as recited in claim 19, wherein the reference PNS data are simulation data generated based on a calibrated model of the neurodynamic responses of nerve fibers to arbitrary external electromagnetic fields.

21. The method as recited in claim 2, wherein the target nerve stimulation requirement comprises exciting one or more target nerve segments.

22. The method as recited in claim 2, wherein the target nerve stimulation requirement comprises blocking excitation of one or more target nerve segments.

23. The method as recited in claim 2, wherein the target nerve stimulation requirement comprises exciting a first set of nerve segments while blocking excitation of a second set of nerve segments.

* * * * *